United States Patent [19]
Zinnen et al.

[11] Patent Number: 6,008,424
[45] Date of Patent: *Dec. 28, 1999

[54] $C_8$ ALKYLAROMATIC HYDROCARBON PRODUCTION USING REVERSIBLE FLOW REACTIVE CHROMATOGRAPHY

[75] Inventors: Herman A. Zinnen, Evanston; Maureen L. Bricker, Buffalo Grove; Charles P. McGonegal, Addison, all of Ill.

[73] Assignee: UOP LLC, Des Plaines, Ill.

[ * ] Notice: This patent is subject to a terminal disclaimer.

[21] Appl. No.: 09/175,033

[22] Filed: Oct. 19, 1998

Related U.S. Application Data

[63] Continuation-in-part of application No. 08/851,354, May 5, 1997, Pat. No. 5,877,373.

[51] Int. Cl.$^6$ .................................................. C07C 5/22
[52] U.S. Cl. ........................ 585/475; 585/470; 585/474
[58] Field of Search ................... 585/470, 474, 585/475

[56] References Cited

U.S. PATENT DOCUMENTS

| | | | |
|---|---|---|---|
| 2,836,633 | 5/1958 | Esmay et al. | 260/671 |
| 3,122,494 | 2/1964 | Brown et al. | 208/63 |
| 3,211,798 | 10/1965 | Burk, Jr. et al. | 260/668 |
| 3,997,620 | 12/1976 | Neuzil | 260/674 SA |
| 3,998,901 | 12/1976 | Neuzil et al. | 260/674 SA |
| 4,028,428 | 6/1977 | Neuzil et al. | 260/674 SA |
| 4,079,094 | 3/1978 | Rosback et al. | 260/674 SA |
| 4,255,607 | 3/1981 | Miyake et al. | 585/805 |
| 5,877,373 | 3/1999 | Zinnen et al. | 585/475 |

FOREIGN PATENT DOCUMENTS

| | | | |
|---|---|---|---|
| 67656/90 | 11/1992 | Australia | C07C 15/42 |
| 2 031 096 | 3/1992 | Canada | 260/685 |

*Primary Examiner*—Walter D. Griffin
*Assistant Examiner*—Thuan D. Dang
*Attorney, Agent, or Firm*—Thomas K. McBride; Frank S. Molinaro; Maryann Maas

[57] ABSTRACT

A process for the transalkylation of benzene, toluene and alkylaromatic hydrocarbons containing nine and ten carbon atoms form alkylaromatic hydrocarbons containing eight carbon atoms has been developed. The fixed bed reaction and adsorption zone contains a transalkylation catalyst and an adsorbent effective to selectively adsorb $C_9$ and $C_{10}$ alkylaromatic hydrocarbon reactants relative to the $C_8$ alkylaromatic hydrocarbon products. Hydrogen and a desorbent are introduced to a first portion of the zone and an effluent containing at least one $C_8$ alkylaromatic hydrocarbon product is withdrawn from a second portion of the zone. After a period of time, the desorbent is redirected to the second portion of the zone and concurrently the effluent containing at least one $C_8$ alkylaromatic hydrocarbon product is withdrawn from the first portion of the zone. The alternation of introducing the desorbent to a first portion and then a second portion of the zone while concurrently withdrawing the effluent from the second portion and then the first portion of the zone is continued, thereby retaining the $C_9$ and $C_{10}$ alkylaromatic hydrocarbons within the zone until they are consumed.

16 Claims, 6 Drawing Sheets

C₈ ALKYLAROMATIC HYDROCARBON PRODUCTION USING REVERSIBLE FLOW REACTIVE CHROMATOGRAPHY

CROSS REFERENCE TO RELATED APPLICATION

This application is a continuation-in-part of our application, application Ser. No. 08/851,354 filed May 5, 1997 now U.S. Pat. No. 5,877,373, all of which is hereby incorporated by reference.

BACKGROUND OF THE INVENTION $C_8$ alkylaromatic hydrocarbons are generally considered to be valuable products, and para-xylene in particular is in high demand. On the other hand, $C_9$ and $C_{10}$ alkylaromatic hydrocarbons are not nearly as valuable but are typically produced as a byproduct in the same aromatic production processes used to produce $C_8$ alkylaromatic hydrocarbons. Various approaches have been used to convert the less valuable $C_9$ and $C_{10}$ alkylaromatic hydrocarbons into $C_8$ alkylaromatic hydrocarbons. One popular approach has been to transalkylate $C_9$ and $C_{10}$ alkylaromatic hydrocarbons along with benzene or toluene to form the $C_8$ alkylaromatic hydrocarbons. Specifically, trimethylbenzenes and tetramethylbenzenes have been transalkylated along with benzene and toluene to form xylenes. However, transalkylation reactions are equilibrium limited and the product contains a mixture of unreacted $C_9$ and $C_{10}$ alkylaromatic hydrocarbons along with the desired $C_8$ alkylaromatic hydrocarbons. To increase conversion, commercial processes have utilized a two-stage design with the first stage being a fixed bed reactor and the second stage being a separation unit. Unreacted $C_9$ and $C_{10}$ alkylaromatic hydrocarbons present in the reactor product stream are separated and recycled to the reactor; see for example U.S. Pat. No. 3,211,798.

The present invention makes use of reversible flow reactive chromatography to perform the transalkylation. Reactive chromatography in general allows for concurrent reaction and separation of the unconsumed reactants from products, thereby extending product yields beyond thermodynamic equilibrium limitations. Reactive chromatography has been applied to other classes of chemical reactions; see for example U.S. Pat. No. 3,122,494 which describes an isomerization process having two sub-beds containing a mixture of catalyst and adsorbent where the feed is introduced between the two sub-beds and the desorbent introduction is alternated between the first sub-bed and the second sub-bed. The adsorbent must selectively adsorb straight-chain hydrocarbons to the substantial exclusion of non-straight-chain hydrocarbons.

The present invention expands the application of reversible flow reactive chromatography to an entirely new class of chemical reactions, the transalkylation of alkylaromatic hydrocarbons. U.S. Pat. No. 2,836,633 describes alkylation of aromatic hydrocarbons using a catalyst supported on an adsorbent, but the purpose of using the adsorbent support was to increase the activity of the catalyst, not to perform an actual separation. CA2031096 and AU9067656-A describe an alkylation process where an alkene is adsorbed on a dry cationic exchange resin in its hydrogen form and is simultaneously reacted with an aromatic hydrocarbon. The present invention uses reversible flow and the combination of catalyst and adsorbent in a single zone both to effect transalkylation and to concurrently separate the unconsumed $C_9$ and $C_{10}$ alkylaromatic hydrocarbons from the $C_8$ alkylaromatic hydrocarbon products.

SUMMARY OF THE INVENTION

The purpose of the invention is to transalkylate benzene, toluene, and alkylaromatic hydrocarbons containing 9 and 10 carbon atoms and at least one methyl or ethyl group to form alkylaromatic hydrocarbons containing 8 carbon atoms. The alkylaromatic hydrocarbon reactants are introduced to a fixed bed reaction and adsorption zone operating under conditions effective for transalkylation and selective adsorption, and containing a catalyst effective to transalkylate the benzene and alkylaromatic hydrocarbon reactants and an adsorbent effective to selectively adsorb $C_9$ and $C_{10}$ alkylaromatic hydrocarbon reactants relative to the $C_8$ alkylaromatic hydrocarbon products. Hydrogen and a desorbent capable of desorbing the $C_9$ and $C_{10}$ alkylaromatic hydrocarbons from the adsorbent is introduced to a first portion of the reaction and adsorption zone and an effluent containing at least one $C_8$ alkylaromatic hydrocarbon product is withdrawn from a second portion of the reaction and adsorption zone. Unreacted toluene and benzene will also be removed in the effluent. After a period of time, the desorbent is redirected to the second portion of the reaction and adsorption zone and concurrently the effluent containing at least one $C_8$ alkylaromatic hydrocarbon product is withdrawn from the first portion of the reaction and adsorption zone. The alternation of introducing the desorbent to a first portion and then a second portion of the reaction and adsorption zone while concurrently withdrawing the effluent from the second portion and then the first portion of the reaction and adsorption zone is continued, thereby retaining the $C_9$ and $C_{10}$ alkylaromatic hydrocarbon reactants within the reaction and adsorption zone until they are consumed.

A specific embodiment of the invention is one where the feed is introduced to the same portion of the reaction and adsorption zone as the desorbent is introduced, with the feed being introduced in a pulsed manner. Periodically, the location of the feed and desorbent input is alternated between a first portion of the zone and a second portion of the zone. Another specific embodiment of the invention is one where the feed and desorbent are both continuously introduced to the reaction and adsorption zone. The feed is introduced at a location so that the zone is symmetrically disposed about the feed with respect to size, flow capacity, and adsorbent and catalyst distribution thereby dividing the zone into two equivalent portions. The position of the feed input remains constant while periodically the desorbent input is alternated between the first portion of the zone and the second portion of the zone. In each of the above embodiments, an effluent stream containing at least one $C_8$ alkylaromatic hydrocarbon product is withdrawn from that portion of the zone where the desorbent is not being introduced.

DETAILED DESCRIPTION OF THE INVENTION

This invention is a process for overcoming the equilibrium limitations of a monocyclic $C_8$ alkylaromatic hydrocarbon production process using reversible flow reactive chromatography. The invention involves such molecular rearrangement as the transfer of the methyl groups of toluene to form benzene and xylenes or the transfer of the methyl groups of toluene, trimethylbenzenes, and tetramethylbenzenes to produce xylenes. Such reactions are referred to herein as transalkylation. In addition, $C_9$ and $C_{10}$ alkylaromatic hydrocarbon reactants may undergo other types of reactions. For example, ethyl groups may be transalkylated or dealkylated, which is sometimes referred to as disproportionation, but is also referred to herein as transalkylation.

In general terms, the invention is carried out by introducing benzene, toluene, or a mixture thereof and a $C_9$ or $C_{10}$ alkylaromatic hydrocarbon reactant containing at least one methyl or ethyl group, or a mixture thereof, to a zone containing both a catalyst effective for transalkylation and an adsorbent capable of adsorbing the $C_9$ and $C_{10}$ alkylaromatic hydrocarbon reactants relative to the $C_8$ alkylaromatic hydrocarbon products. Hydrogen and a desorbent are also introduced to the zone containing the catalyst and adsorbent. The reactants are transalkylated with the aid of the catalyst and the typically desired $C_8$ alkylaromatic hydrocarbon products consist of otho-, meta-, and para-xylenes, with the most desired product being para-xylene. Depending upon the application, ethylbenzene may also be a desired $C_8$ alkylaromatic hydrocarbon product. The products are immediately separated from any unreacted $C_9$ and $C_{10}$ alkylaromatic hydrocarbons since the adsorbent is chosen to selectively adsorb the $C_9$ and $C_{10}$ alkylaromatic hydrocarbon reactants. The $C_8$ alkylaromatic hydrocarbons will be least adsorbed by the adsorbent relative to the $C_9$ and $C_{10}$ alkylaromatic hydrocarbons and so will be carried unhindered with the flow of the desorbent and removed from the zone. The product stream removed from the zone will contain a mixture of desorbent, $C_8$ alkylaromatic hydrocarbons, and any benzene and unreacted toluene.

Due to the dynamic equilibrium of the adsorbent with components constantly being adsorbed and desorbed, a band of $C_9$ and $C_{10}$ alkylaromatic hydrocarbon reactants will gradually move through the zone and will eventually reach the point where the products are being withdrawn from the zone. To avoid contaminating the product effluent with the band of $C_9$ and $C_{10}$ alkylaromatic hydrocarbon reactants, the introduction of the desorbent is changed to a different location in the zone so that the flow of desorbent is now reversed through the zone. The location where the product effluent is withdrawn is also moved to remain downstream of the desorbent. Due to the continuous separation and removal of the $C_8$ alkylaromatic hydrocarbon products, the thermodynamic equilibrium constraint of a static system is no longer a limiting factor, and the reaction continues thereby resulting in a much greater conversion to valuable $C_8$ alkylaromatic hydrocarbons and para-xylene in particular. Also, the least valuable reactants, the $C_9$ and $C_{10}$ alkylaromatic hydrocarbons, are contained within the reaction and adsorption zone until consumed to form more valuable products.

As discussed above, it is a requirement that the reaction and adsorption zone contain a catalyst effective for aromatic transalkylation. Such catalysts are well known in the art and suitable catalysts include, but are not limited to, mordenite, zeolite Beta, ZSM-5, and dealuminated zeolite Y having a $SiO_2/Al_2O_3$ ratio in the range of from about 5 to about 25, sulfated zirconia, tungstated zirconia, and sulfated and tungstated zirconia. The dealuminated zeolite Y catalyst may be further ion exchanged with a Group IIA element, a Group IB element, or a Group VIII element or a mixture thereof. Some of these catalysts are described, and further references provided, in Meier, W. M.; Olson, D. H.; Baerlocher, Ch. *Atlas of Zeolite Structure Types*, 4th Edition, Elsevier: Boston, 1996, pp. 152–153, 62–63, 146–147, and 104–105. Also, see generally, Kirk-Othmer *Encyclopedia of Chemical Technology*, 4th ed.; Kroschwitz, J. I., Howe-Grant, M., Eds.; John Wiley & Sons: New York, vol. 4, pp. 83–84. A preferred catalyst is one containing mordenite. Depending upon the composition of the feed, several different catalysts may be combined in order to accomplish the catalysis function.

When choosing a catalyst, the operating temperature of the adsorbent that will be used must be considered. Both the adsorbent and the catalyst must be able to perform their respective functions at the same operating temperature. The reaction and adsorption zone may be operated at $C_8$ alkylaromatic production operating conditions including temperatures ranging from 150° C. to 300° C. and pressures from atmospheric to 600 psig (4,137 kPag). The temperatures specified here are lower than traditional operating temperatures since equilibrium favors $C_8$ alkylaromatic hydrocarbon formation at lower temperatures. The operating conditions should be chosen so that all components are in the same phase, gas or liquid. The gas phase allows higher mass transfer while the liquid phase provides higher adsorbent loading. Since many of the suitable adsorbents perform better at lower temperatures when using a physical mixture of adsorbent and catalyst, the preferred catalyst is mordenite due to its activity at lower temperatures. Ancillary added benefits of operating the process at a lower temperature include potentially extending the catalyst life and reducing the cost of the physical vessel(s) making up the reaction and adsorption zone.

It is also required that the reaction and adsorption zone contain an adsorbent. The adsorbent is selected to have either a pore size capable of retaining $C_9$ and $C_{10}$ alkylaromatic hydrocarbon reactants but not the $C_8$ alkylaromatic hydrocarbon products or to have a selectivity for $C_9$ and $C_{10}$ alkylaromatic hydrocarbon reactants. In other words, the adsorbent must adsorb $C_9$ and $C_{10}$ alkylaromatic hydrocarbons relative to $C_8$ alkylaromatic hydrocarbons at the reactor operating conditions. Any adsorbent meeting this criteria may be used in the process. Examples of suitable adsorbents include, but are not limited to, zeolite Beta, zeolite X, zeolite Y, and dealuminated zeolite Y having a $SiO_2/Al_2O_3$ ratio in the range of from about 5 to about 25. Zeolite Y may be ion exchanged with calcium, sodium, strontium, a Group IB element, a Group VIII element, or mixtures thereof and used successfully in the present invention. Dealuminated zeolite Y having a $SiO_2/Al_2O_3$ ratio in the range of from about 5 to about 25, and preferably from about 6 to about 12, may be ion exchanged with calcium, potassium, sodium, strontium, a Group IB element, a Group VIII element, or mixtures thereof and used successfully in the present invention. Some of these adsorbents are described, and further references provided, in Meier, W. M.; Olson, D. H.; Baerlocher, *Ch. Atlas of Zeolite Structure Types,* 4th *Edition,* Elsevier: Boston, 1996, pp. 62–63 and 104–105. See also, U.S. Pat. No. 4,940,830 which is incorporated by reference. A preferred adsorbent is zeolite Y ion exchanged with sodium, and a most preferred adsorbent is zeolite Y-54 ion exchanged with sodium and strontium; see Example 5. As with the catalyst, two or more adsorbents may be used within the same reaction and adsorption zone.

Figure 3:
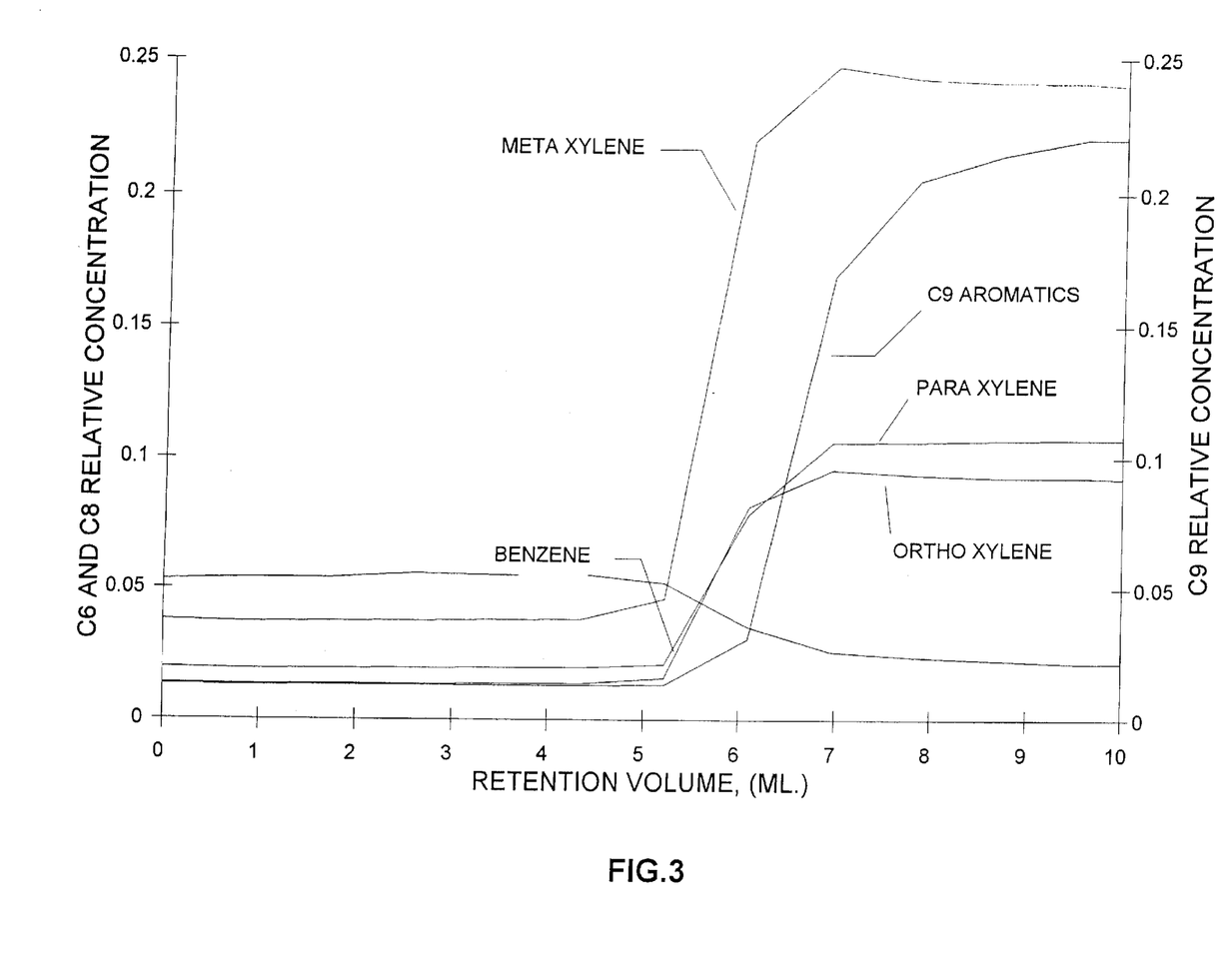
FIG. 3 is the chromatographic plot of the concurrent transalkylation of 1,3,5-trimethylbenzene and separation of the $C_8$ alkylaromatic hydrocarbon products using zeolite Beta as both the catalyst and adsorbent as described in Example 3. Each individual isomer of the $C_8$ alkylaromatic hydrocarbons is plotted and the $C_9$ alkylaromatic hydrocarbons are summed and the sum of the concentrations is plotted.

Particular adsorbents may retain the individual species of $C_8$ alkylaromatic hydrocarbons differently, which may be advantageous in specific applications. For example, zeolite Beta has greater selectivity for para-xylene and ortho-xylene as compared to meta-xylene. Therefore, the first eluting portion of the $C_8$ alkylaromatic hydrocarbon fraction is particularly enriched in meta-xylene as compared to para-xylene and ortho-xylene; see Example 3. The flow reversal may be timed so that the product stream is enriched in meta-xylene as compared to an equilibrium mixture of all xylene isomers.

The catalyst and adsorbent may be present in the fixed bed reaction and adsorption zone in a variety of ways with the catalyst to adsorbent volume ratio ranging from about 0.01 to about 1.0. It is preferred that the particles be present in a mixture and it is most preferred that the mixture be a homogeneous mixture of adsorbent and catalyst particles which is distributed throughout the zone. Although less preferred, it is possible that the particles may be structured in alternating layers, sections, or cells as is known in the reactive chromatography art. For example, a vessel could contain a thin layer of catalyst followed by a thin layer of adsorbent with the pattern repeating throughout the vessel. The zone itself may be all contained within a single vessel or may be composed of a series of two or more sub-beds that are sequentially connected. It is important, however, that the catalyst and adsorbent be structured so that the zone is capable of performing reactive chromatography where the products are rapidly separated from reactants. Therefore, it would be unacceptable to have, for example, the zone consist of only two sub-beds, one containing only catalyst and the other containing only adsorbent, or only three sub-beds with a catalyst-only sub-bed between two adsorbent-only sub-beds. To perform reactive chromatography the catalyst and adsorbent must be of sufficient integration with one another so that the equilibrium limitations of a fixed bed system are overcome. Furthermore, if the catalyst and adsorbent were not sufficiently integrated the product $C_8$ alkylaromatic hydrocarbons may undergo reversion to reactants wherever the zone contains predominantly catalyst. Such reversion is undesirable and is to be avoided.

Note that in the present invention zeolite Beta and dealuminated zeolite Y are able to function as both an adsorbent and as a catalyst. Therefore, the invention could be successfully practiced by using only zeolite Beta or only dealuminated zeolite Y in the reaction and adsorption zone. Zeolite Beta or dealuminated zeolite Y would both catalyze the transalktylation reaction and adsorb the $C_9$ and $C_{10}$ alkylaromatic hydrocarbons. In particular applications, using only one type of particle may be advantageous since the overall loading, operation, regeneration, and maintenance of the reaction and adsorption zone may be simplified. Because of these advantages, it is preferred to use a single type of particle that is able to function as both an adsorbent and as a catalyst.

For catalyst stability, hydrogen may be introduced into the reaction and adsorption zone. The hydrogen may be introduced in a variety of ways, any of which would be appropriate so long as sufficient hydrogen is present where needed to provide the catalyst stabilizing function. The hydrogen to hydrocarbon mole ratio in the reaction and adsorption zone should be within a range from about 0.1 to about 6. The hydrogen may be introduced with, or independently of, the feed or the desorbent, and it may be introduced continuously or in a pulsed manner. For convenience, it is preferred that the hydrogen be introduced with and in the same manner as the desorbent. However, the hydrogen must be introduced in a fashion that does not significantly disturb the chromatography of the separation.

The desorbent must be capable of desorbing the $C_9$ and $C_{10}$ alkylaromatic hydrocarbon reactants. Examples of acceptable reactive desorbents include benzene and toluene. Non-reactive desorbents which could be fractionated from the effluent and recycled for reuse are also contemplated. It is preferred that the desorbent be capable of entering into the transalkylation reaction since the result would be an increase in the amount of $C_8$ alkylaromatic hydrocarbon products formed. For example, benzene or toluene desorbent would enter into the transalkylation reaction with the $C_9$ and $C_{10}$ alkylaromatic hydrocarbons and form additional $C_8$ alkylaromatic hydrocarbon products. Toluene has the additional benefit of being able to undergo transalkylation (sometimes referred to as toluene disproportionation) where two moles of toluene react to form one mole of benzene and one mole of xylene. Therefore, the preferred desorbents are benzene and toluene or a mixture thereof, with toluene being the most preferred desorbent. While a nonreactive desorbent may perform the desorbent function, the incidental increase in product amount achieved with benzene and toluene would be foregone.

The feed to the process contains a benzene or toluene reactant and at least one reactant being a $C_9$ or $C_{10}$ alkylaromatic hydrocarbon containing at least one methyl or ethyl group. References herein to "$C_9$ or $C_{10}$ alkylaromatic hydrocarbon" are to be understood as limited to those having at least one methyl or ethyl group. If the desorbent is benzene or toluene, the feed need only contain at least one $C_9$ or $C_{10}$ alkylaromatic hydrocarbon reactant. The preferred $C_9$ and $C_{10}$ alkylaromatic hydrocarbon reactants are trimethylbenzenes and tetramethylbenzenes. Examples of specific suitable alkylaromatic hydrocarbon reactants include, but are not limited to, toluene, 1,3,5-trimethylbenzene, 1,2,4-trimethylbenzene, 1,2,3-trimethylbenzene, and the tetramethylbenzene isomers. Other alkylaromatic hydrocarbons such as methylethyl benzenes and propylbenzenes may be present in the feed, but may not contribute to the formation of valuable xylene products. However, methylethyl benzenes present in the feed would contribute to the formation of ethylbenzene, which may be a desired product in certain applications. The feed should not contain components that would significantly alter the capacities or selectivities of the desorbent or that would deactivate the catalyst. The feed may also be an effluent from an aromatics complex such as a Platforming product after unreacted alkanes and the desired $C_8$ alkylaromatic hydrocarbons have been removed. The product stream withdrawn from the reaction and adsorption zone will contain desorbent and the desired $C_8$ alkylaromatic hydrocarbon products which are usually, ortho- meta- and para-xylenes. The product stream would also contain any benzene and unreacted toluene. If methylethyl benzenes were present in the feed, a further desired component of the product stream may be ethylbenzene.

The invention encompasses two different preferred operational embodiments. In a first preferred embodiment both the desorbent and the feed are introduced to the reaction and adsorption zone at a first end of the zone in a co-current flow mode. The feed is introduced as a pulse and the desorbent may be introduced continuously or the desorbent may be stopped momentarily while the pulse of feed is introduced. The reactants in the feed contact the catalyst and undergo transalkylation to form $C_8$ alkylaromatic hydrocarbon products. Any unreacted $C_9$ and $C_{10}$ alkylaromatic components are adsorbed by the adsorbent. Unreacted benzene, toluene, and the $C_8$ alkylaromatic hydrocarbon products are relatively unadsorbed and so are carried unhindered with the desorbent flow. At a second end of the reaction and adsorption zone, unreacted benzene and toluene and the product $C_8$ alkylaromatic hydrocarbon are removed in a product stream as a mixture with desorbent.

The $C_9$ and $C_{10}$ alkylaromatic hydrocarbon reactants are continuously being adsorbed and desorbed and therefore gradually move through the zone with the desorbent flow. As the $C_9$ and $C_{10}$ alkylaromatic hydrocarbon reactants are desorbed, they will contact the catalyst and benzene and toluene reactants and will continue to undergo transalkylation. Eventually the front of $C_9$ and $C_{10}$ alkylaromatic hydrocarbon reactants will approach the second end of the zone where the product stream is being removed. At this time, the flow in the zone is reversed with the feed now being pulsed in at the second end, the desorbent also being introduced at the second end, and the product stream being removed from the first end. The concentration of $C_9$ and $C_{10}$ alkylaromatic hydrocarbon reactants is now in the region of the zone adjacent to the feed input and will not contaminate the product stream. Furthermore, the $C_9$ and $C_{10}$ alkylaromatic hydrocarbon reactants continue to remain in the zone and are able to contact the catalyst and other reactants to form additional $C_8$ alkylaromatic hydrocarbon products eliminating the need for recycle and reducing reactant waste. The process continues with the periodic reversal of fluid flow by alternating the input location of the desorbent and feed from one end of the zone to another and back.

The pulses of feed and the reversal of fluid flow in the zone are timed and the flowrates of the feed and desorbent are controlled so that the $C_9$ and $C_{10}$ alkylaromatic hydrocarbon reactants do not contaminate the product stream and remain within the zone until they are reacted. A portion of the benzene or toluene desorbent may also be converted to $C_8$ alkylaromatic hydrocarbon products, but due to the volume of desorbent used, desorbent will be present in the product stream as is typical of a chromatographic process.

A bleed stream may be used to prevent the buildup of highly adsorbed material. The bleed stream is of a minimal flowrate, greatly reduced as compared to the flowrates of other streams of the zone, may be continuous flow or intermittent flow, and may be removed from the zone in a variety of ways. The bleed stream may be removed at the same location as the product stream and timed so that the highly adsorbed materials are removed. The bleed may be positioned within the zone and may consist of a single conduit or multiple exit conduits, each of which is activated as the fraction of interest passes adjacent to an exit conduit.

In the most preferred operational embodiment of the invention, both the feed and desorbent are continuously introduced to the reaction and adsorption zone. Like the embodiment above, the desorbent is introduced to a first end of the reaction and adsorption zone. However, in this embodiment, the feed is introduced at about the center of the reaction and adsorption zone. It is important that the reaction and adsorption zone be symmetrically disposed about the point of feed introduction with respect to the size of the zone, the flow capacity of the zone, and especially the catalyst and adsorbent distribution within the zone. For example, if the zone were a series of six equally sized sequentially connected sub-beds each containing a homogeneous mixture of catalyst and adsorbent, the feed introduction point should be between the third and fourth sub-bed. The location of the feed remains constant during the process and can be described as dividing the zone into two equivalent portions.

Both the feed and the desorbent are continuously introduced to the reaction and adsorption zone. The reactants in the feed contact the catalyst and undergo transalkylation to form $C_8$ alkylaromatic hydrocarbon products. $C_9$ and $C_{10}$ alkylaromatic hydrocarbon reactants are adsorbed by the adsorbent and the $C_8$ alkylaromatic hydrocarbon compounds are relatively unadsorbed and so are carried unhindered with the desorbent flow. At a second end of the reaction and adsorption zone, the $C_8$ alkylaromatic hydrocarbon products are removed in a product stream as a mixture with desorbent. As in the above embodiment, the $C_9$ and $C_{10}$ alkylaromatic hydrocarbon reactants are continuously being adsorbed and desorbed and therefore gradually move through the zone with the desorbent flow. As the $C_9$ and $C_{10}$ alkylaromatic hydrocarbon reactants are desorbed, they will contact the catalyst and other reactants and will continue to undergo transalkylation. Eventually the front of $C_9$ and $C_{10}$ alkylaromatic hydrocarbon reactants will approach the second end of the zone where the product stream is being removed. At this time, the flow in the zone is reversed by introducing the desorbent at the second end of the zone instead of at the first end and removing the product stream from the first end of the zone. The location of the feed input remains constant. The concentration of $C_9$ and $C_{10}$ alkylaromatic hydrocarbon reactants is now in the region of the zone adjacent to the desorbent input and will not contaminate the product stream, and the $C_9$ and $C_{10}$ alkylaromatic hydrocarbon reactants remain in the zone and are able to contact the catalyst and other reactants to form additional $C_8$ alkylaromatic hydrocarbon products. The process continues with the periodic reversal of desorbent flow to keep the $C_9$ and $C_{10}$ alkylaromatic hydrocarbon reactants within the zone until they are converted to $C_8$ alkylaromatic hydrocarbon products. A low flowrate bleed stream may be taken to reduce the buildup of highly adsorbed material. The preferred location for the bleed stream is in the vicinity of the feed input. The most preferred location for the bleed stream is in the vicinity of, but upstream to, the feed input. The product stream from each of the embodiments discussed above may be purified by such techniques as fractionation or crystallization.

While the above-described embodiments are the preferred embodiments, other modes of operation are successful, such as introducing the feedstock in a pulsed mode to a central location within the reaction and adsorption zone.

The following examples are presented in illustration of this invention and are not intended as an undue limitation on the generally broad scope of the invention as set out in the appended claims.

EXAMPLE 1

Two 70 mL columns were loaded with a homogeneous mixture of 20–40 mesh catalyst and adsorbent. The catalyst was H-mordenite bound with alumina and the adsorbent was Na—Y zeolite bound with clay. The columns were placed in a heated enclosure at 250° C. and maintained at process pressure of 50 psig using back pressure regulators. 1,3,5-trimethylbenzene feed, toluene desorbent, and hydrogen were directed into the columns at measured rates. The effluent of the system was condensed and the liquid product was analyzed by gas chromatography to obtain the composition of the product. For each experiment, the system was operated first in a fixed bed mode and then in a reversible flow mode. Different process parameters were chosen for each experiment and are noted in Table 1.

The process parameters and results are listed in Table 1. "A" is the selective co-current pore volume rate, "F" is the feed volume rate, "D" is the desorbent volume rate, $H_2$/HC is the hydrogen to hydrocarbon mole ratio, "ACR" is the adsorbent:catalyst ratio, "%$C_9$ Conversion" is the percent of feed material that was converted from $C_9$ alkylaromatic hydrocarbons to products, and $C_8/C_9$ is the ratio of $C_8$ alkylaromatic hydrocarbons to $C_9$ alkylaromatic hydrocarbons in the product.

TABLE 1

| Mode | Cycle Time (min.) | A/F | D/F | $H_2$/HC | ACR | % $C_9$ Conversion | $C_8/C_9$ |
|---|---|---|---|---|---|---|---|
| Experiment 1 | | | | | | | |
| Fixed Bed | — | — | 2.08 | 0.92 | 2.88 | 25.9 | 1.03 |
| Reversible Flow | 44 | 2.7 | 2.08 | 0.92 | 2.88 | 59.9 | 2.90 |
| Experiment 2 | | | | | | | |
| Fixed Bed | — | — | 3.97 | 0.81 | 2.88 | 19.9 | 0.68 |
| Reversible Flow | 30 | 3.98 | 3.97 | 0.81 | 2.88 | 43.5 | 1.23 |

Two 70 mL columns were next loaded with a single 20–40 mesh compound which is capable of functioning both as a catalyst and as an adsorbent, zeolite Beta. Three more experiments were conducted using the same procedure and conditions as outlined above. The process parameters and results are listed in Table 2. Note that "ACR" values are not applicable since the entire bed volume is both catalyst and adsorbent.

TABLE 2

| Mode | Cycle Time (min.) | A/F | D/F | $H_2$/HC | % $C_9$ Conversion | $C_8/C_9$ |
|---|---|---|---|---|---|---|
| Experiment 3 | | | | | | |
| Fixed Bed | — | — | 1.97 | 2.08 | 54.8 | 3.24 |
| Reversible Flow | 30 | 5.80 | 1.97 | 2.08 | 61.0 | 3.36 |
| Experiment 4 | | | | | | |
| Fixed Bed | — | — | 3.97 | 0.81 | 35.4 | 1.40 |
| Reversible Flow | 30 | 11.20 | 3.94 | 3.10 | 63.9 | 3.60 |
| Experiment 5 | | | | | | |
| Fixed Bed | — | — | 4.0 | 1.53 | 37.7 | 1.60 |
| Reversible Flow | 24 | 7.0 | 4.0 | 1.53 | 59.1 | 1.64 |

As Tables 1 and 2 show, in each experiment the reversible flow mode yields a significantly higher conversion of feed hydrocarbon than that achieved in the fixed bed mode. Furthermore, the relative ratio of $C_8$ alkylaromatic hydrocarbons to $C_9$ alkylaromatic hydrocarbons is larger in the reversible flow mode than in the fixed bed mode, which may reduce the expense of downstream separation.

EXAMPLE 2

Figure 1:
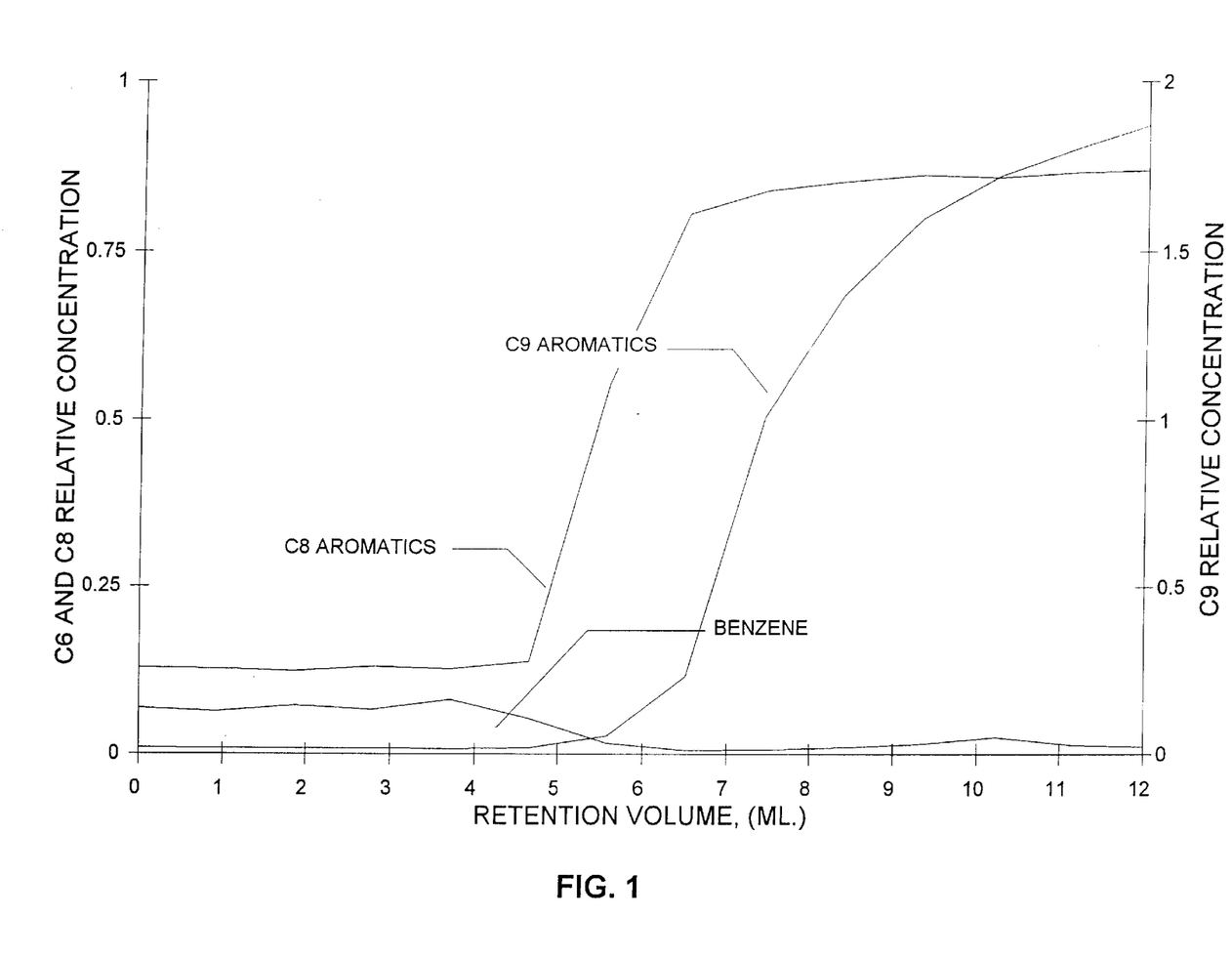
FIG. 1 is the chromatographic plot of the concurrent transalkylation of 1,2,4-trimethylbenzene and separation of the $C_8$ alkylaromatic hydrocarbon products using dealuminated zeolite Y as both the catalyst and adsorbent as described in Example 2. The $C_8$ alkylaromatic hydrocarbons are summed and the sum of the concentrations is plotted. Similarly, the $C_9$ alkylaromatic hydrocarbons are summed and the sum of the concentrations is plotted.

A 70 mL column was loaded with 34.9 grams of a single 20–40 mesh compound which is capable of functioning both as a catalyst and as an adsorbent, dealuminated zeolite Y. The column was placed in a heated enclosure at 250° C. and maintained at process pressure of 28 psig using back pressure regulators. Toluene desorbent and hydrogen were directed into the columns at measured rates. A 20 mL pulse of 1,2,4-trimethylbenzene feed was introduced and the desorbent flow was resumed. The effluent of the system was condensed and analyzed by gas chromatography to obtain the composition of the effluent. FIG. 1 shows the concentration profiles of the effluent beginning with the background level of toluene desorbent and $C_8$ alkylaromatic hydrocarbons, the background level of $C_8$ alkylaromatic hydrocarbons is due to toluene disproportionation. The concentrations of each individual species in a carbon number class were summed and the sum of the concentrations plotted. A region of effluent enriched in $C_8$ alkylaromatic hydrocarbons elutes prior to a region enriched in $C_9$ alkylaromatic hydrocarbons showing that both transalkylation and separation are occurring.

EXAMPLE 3

Figure 2:
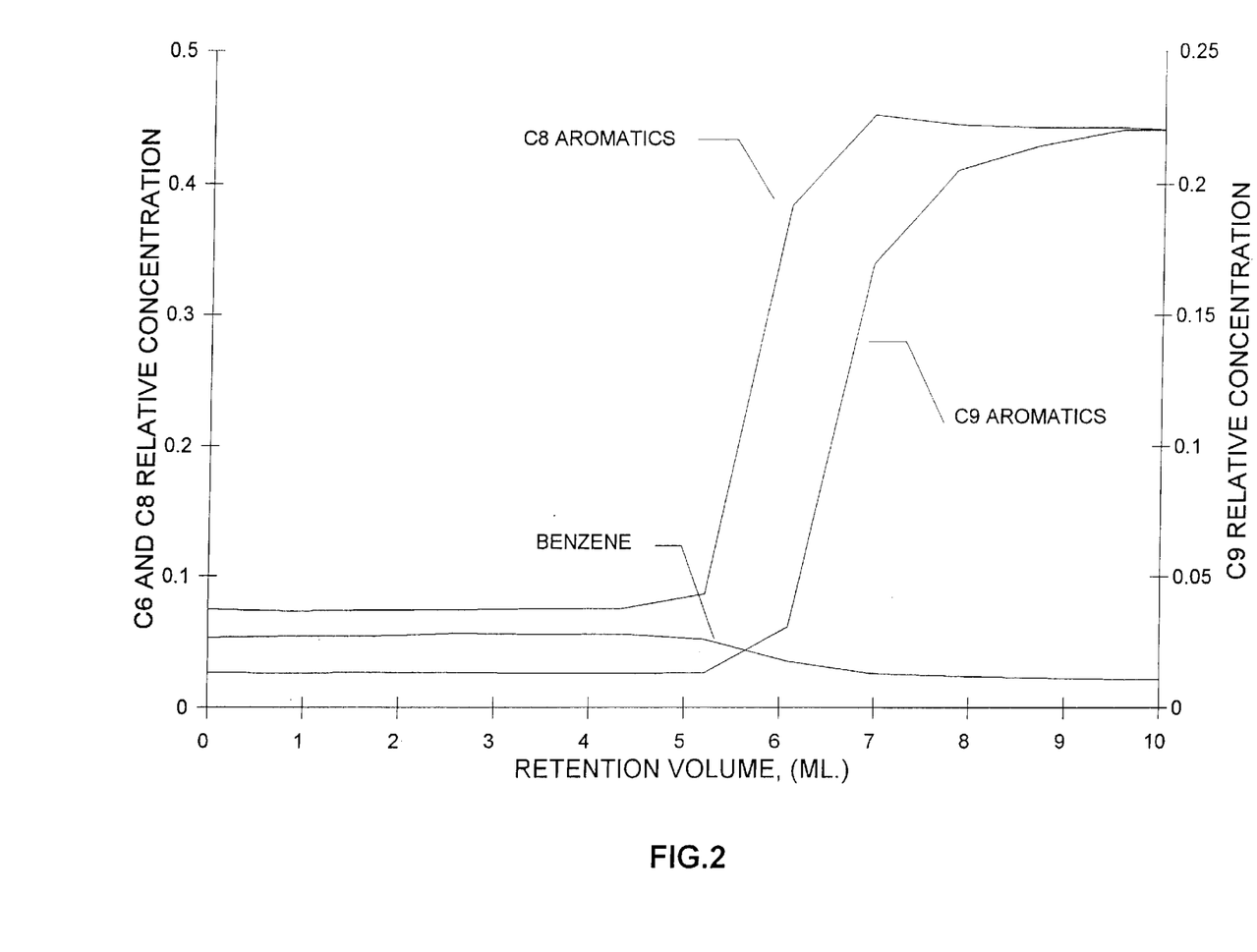
FIG. 2 is the chromatographic plot of the concurrent transalkylation of 1,3,5-trimethylbenzene and separation of the $C_8$ alkylaromatic hydrocarbon products using zeolite Beta as both the catalyst and adsorbent as described in Example 3. The $C_8$ alkylaromatic hydrocarbons are summed and the sum of the concentrations is plotted. Similarly, the $C_9$ alkylaromatic hydrocarbons are summed and the sum of the concentrations is plotted.

A 70 mL column was loaded with 32.1 grams of a single 20–40 mesh compound which is capable of functioning both as a catalyst and as an adsorbent, zeolite Beta. Zeolite Beta has the additional unique characteristic of selectively adsorbing para-xylene and ortho-xylene as compared to meta-xylene. The column was placed in a heated enclosure at 250° C. and maintained at process pressure of 28 psig using back pressure regulators. Toluene desorbent and hydrogen were directed into the columns at measured rates. A 20 mL pulse of 1,3,5-trimethylbenzene feed was introduced and the desorbent flow was resumed. The effluent of the system was condensed and analyzed by gas chromatography to obtain the composition of the effluent. FIG. 2 shows the concentration profiles of the effluent beginning with the background level of toluene desorbent and $C_8$ alkylaromatic hydrocarbons, the background level of $C_8$ alkylaromatic hydrocarbons is due to toluene disproportionation. In FIG. 2, the concentrations of each individual species in a carbon number class were summed and the sum of the concentrations plotted. A region of effluent enriched in $C_8$ alkylaromatic hydrocarbons elutes prior to a region enriched in $C_9$ alkylaromatic hydrocarbons showing that both transalkylation and separation are occurring. Furthermore, because of zeolite Beta's unique characteristic of selectively adsorbing para-xylene and ortho-xylene as compared to meta-xylene, the early eluting portion of the region of effluent enriched in $C_8$ alkylaromatic hydrocarbons is further enriched in meta-xylene. FIG. 3 shows the concentration of the individual $C_8$ alkylaromatic hydrocarbons species, para-xylene, meta-xylene and ortho-xylene, as well as the sum of the $C_9$ alkylaromatic hydrocarbons.

EXAMPLE 4

Figure 4:
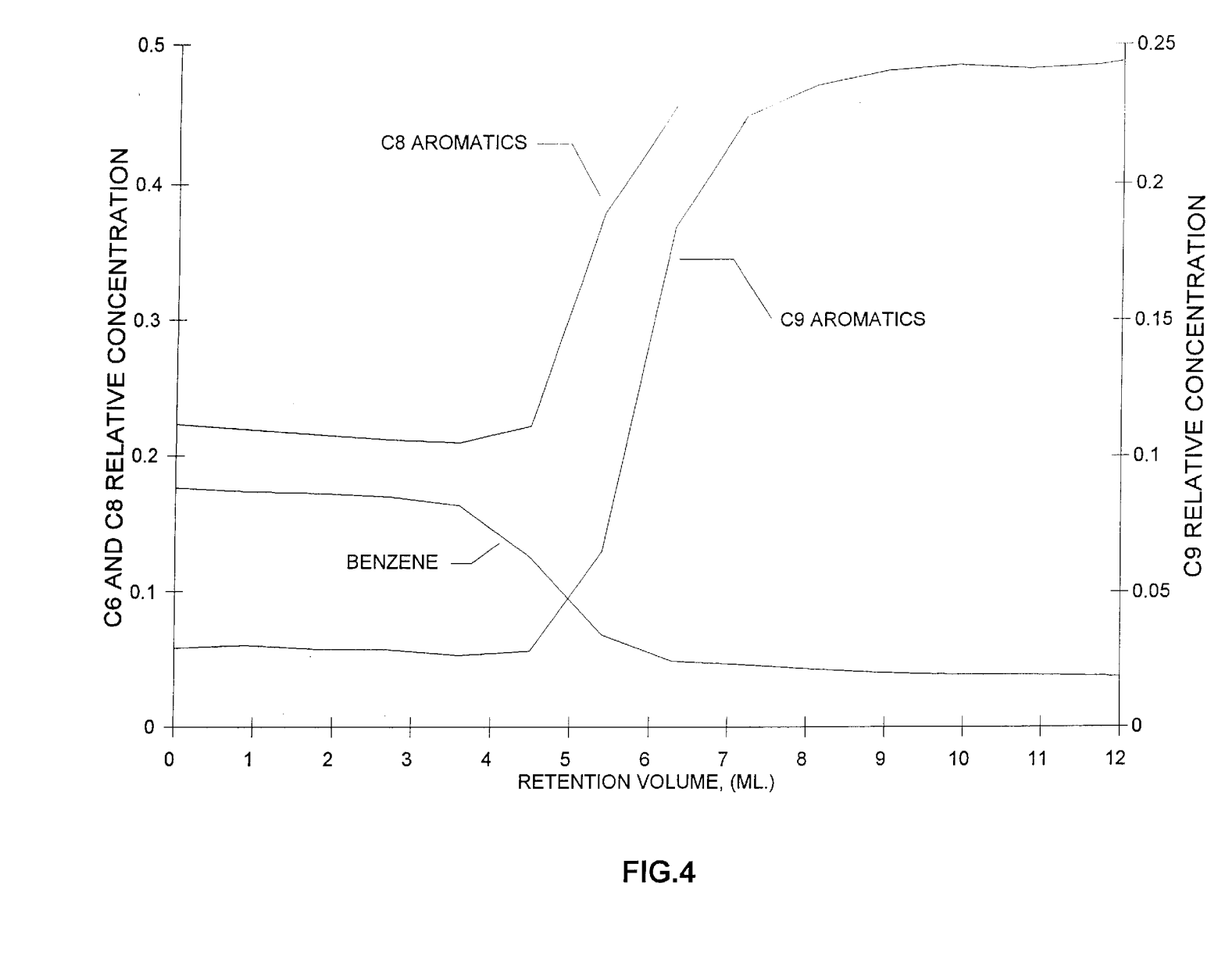
FIG. 4 is the chromatographic plot of the concurrent transalkylation of 1,3,5-trimethylbenzene and separation of the $C_8$ alkylaromatic hydrocarbon products using a homogeneous mixture of H-mordenite bound with alumina catalyst and Na—Y zeolite and bound with clay adsorbent as described in Example 4. The $C_8$ alkylaromatic hydrocarbons are summed and the sum of the concentrations is plotted. Similarly, the $C_9$ alkylaromatic hydrocarbons are summed and the sum of the concentrations is plotted.

A 70 mL column was loaded with a homogeneous mixture of 20–40 mesh catalyst and adsorbent. The catalyst was H-mordenite bound with alumina (12.75 grams) and the adsorbent was Na—Y zeolite bound with clay (24.75 grams). The column was placed in a heated enclosure at 250° C. and maintained at process pressure of 62 psig using back pressure regulators. Toluene desorbent and hydrogen were directed into the columns at measured rates. A 20 mL pulse of a feed containing 50 mass percent toluene and 50 mass percent 1,3,5-trimethylbenzene was introduced and the desorbent flow was resumed. The effluent of the system was condensed and analyzed by gas chromatography to obtain the composition of the effluent. FIG. 4 shows the concentration profiles of the effluent beginning with the background level of toluene desorbent and $C_8$ alkylaromatic hydrocarbons, the background level of $C_8$ alkylaromatic hydrocarbons is due to toluene disproportionation. The concentrations of each individual species in a class were summed and the sum of the concentrations plotted. A region of effluent enriched in $C_8$ alkylaromatic hydrocarbons elutes prior to a region enriched in $C_9$ alkylaromatic hydrocarbons demonstrating that both transalkylation and separation are occurring.

EXAMPLE 5

57 Grams of Na—Y-54 adsorbent containing 10.42 weight percent aluminum (volatile free) and 6.92 weight percent sodium (volatile free) were loaded into a column. 92 Grams of $SrCl_2.H_2O$ were dissolved in 3 liters of water and the resultant solution was circulated through the column for 20 hours at 70° C. and ambient pressure. The solution was drained from the column and the adsorbent was rinsed with 5 L of water. The adsorbent was unloaded from the column and dried in a drying oven for about 16 hours in air at 90° C. The dried adsorbent was analyzed using an inductively coupled argon plasma atomic emission spectrophotometer to have 9.03 weight percent aluminum, 1.77 weight percent sodium, and 4.36 weight percent strontium, all on a volatile free basis.

Figure 5:
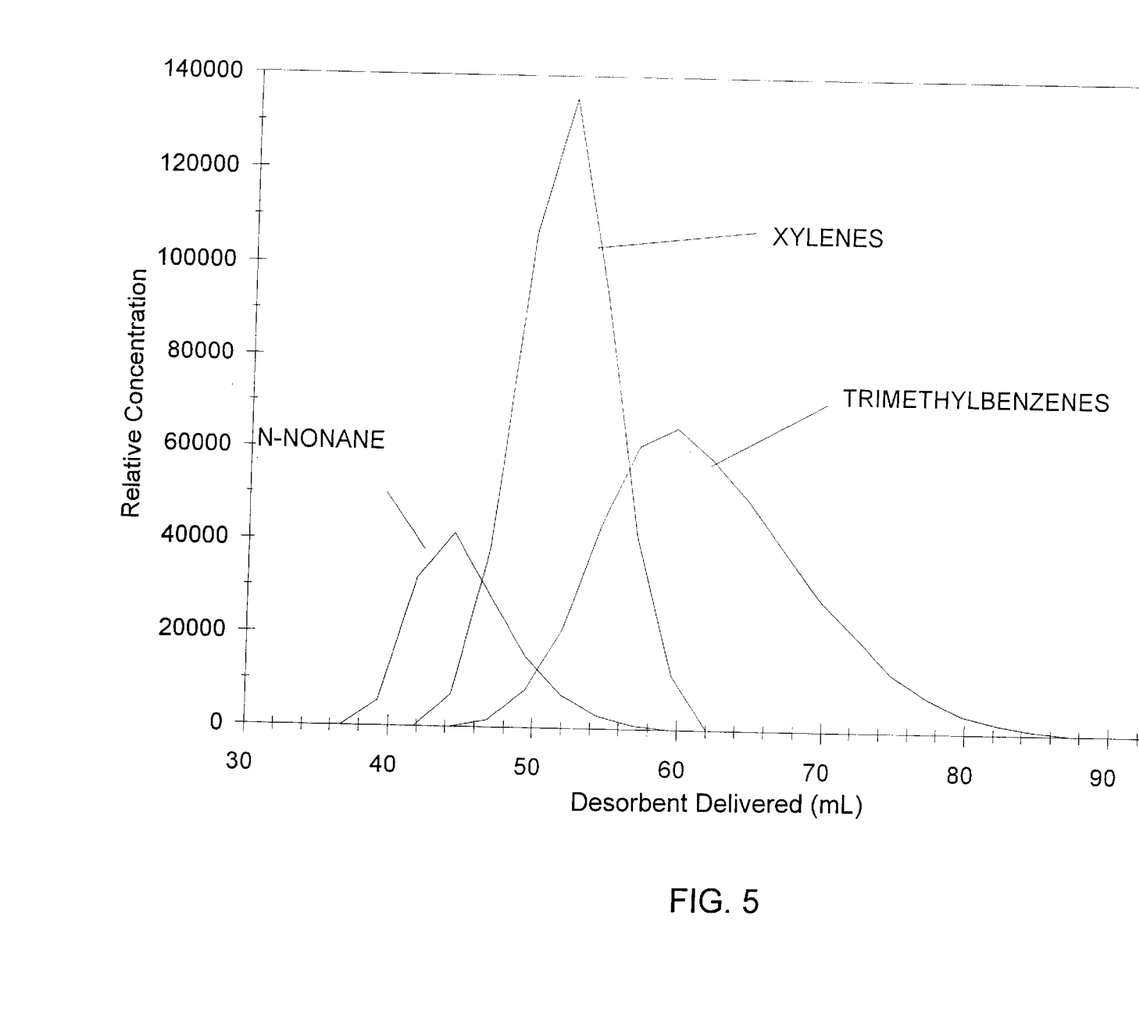
FIG. 5 is the chromatographic plot of the liquid phase separation of the $C_8$ alkylaromatic hydrocarbons from $C_9$ alkylaromatic hydrocarbons using a Na—Y zeolite ion exchanged with strontium adsorbent as described in Example 5. The $C_8$ alkylaromatic hydrocarbons are summed and the sum of the concentrations is plotted. Similarly, the $C_9$ alkylaromatic hydrocarbons are summed and the sum of the concentrations is plotted.

The column containing the dried adsorbent was placed in a heated enclosure at 150° C. and maintained at a pressure of 70 psig using back pressure regulators. Liquid phase toluene desorbent was directed into the columns at measured rates. A liquid phase 2 mL pulse of a feed containing equal parts normal nonane, ethylbenzene, para-xylene, meta-xylene, ortho-xylene, para-methylethylbenzene, meta-methylethylbenzene, ortho-methylethylbenzene, 1,2,3-trimethylbenzene, 1,2,4-trimethylbenzene and 1,3,5-trimethylbenzene was introduced and the desorbent flow was resumed. While in the column, the $C_8$ alkylaromatic hydrocarbons and $C_9$ alkylaromatic hydrocarbons were maintained in the liquid phase. The effluent of the system was analyzed by gas chromatography to obtain the composition of the effluent. FIG. 5 shows the concentration profiles of the effluent beginning with the background level of toluene desorbent and $C_8$ alkylaromatic hydrocarbons, the background level of $C_8$ alkylaromatic hydrocarbons is due to toluene disproportionation. The concentrations of each individual species in a class were summed and the sum of the concentrations plotted. A region of effluent enriched in $C_8$ alkylaromatic hydrocarbons elutes prior to a region enriched in $C_9$ alkylaromatic hydrocarbons demonstrating that separation of the $C_8$ alkylaromatic hydrocarbons from the $C_9$ alkylaromatic hydrocarbons is occurring.

Figure 6:
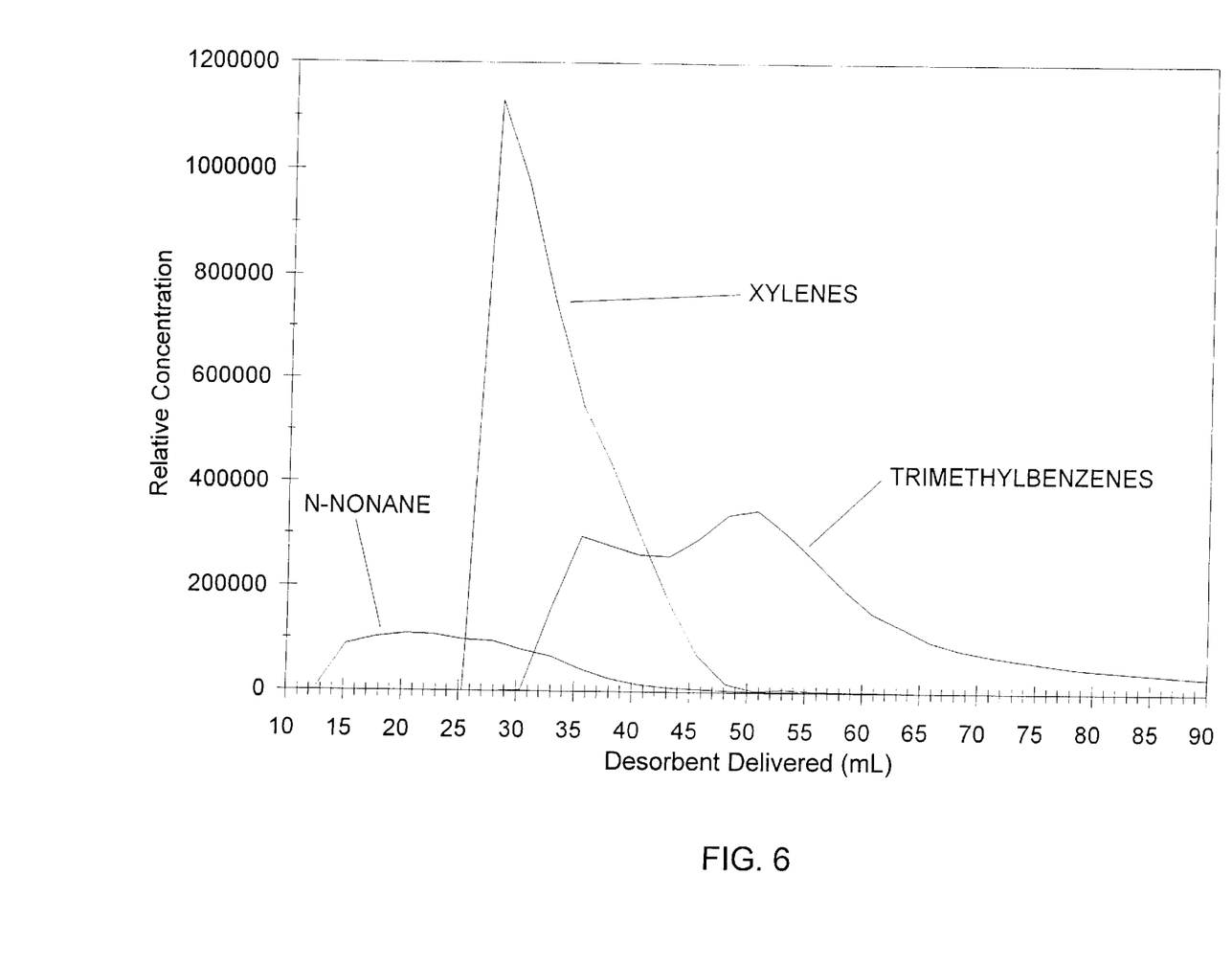
FIG. 6 is the chromatographic plot of the vapor phase separation of the $C_8$ alkylaromatic hydrocarbons from $C_9$ alkylaromatic hydrocarbons using a Na—Y zeolite ion exchanged with strontium adsorbent as described in Example 5. The $C_8$ alkylaromatic hydrocarbons are summed and the sum of the concentrations is plotted. Similarly, the $C_9$ alkylaromatic hydrocarbons are summed and the sum of the concentrations is plotted.

The pulse test was repeated with the components being maintained in the vapor phase. The column containing the dried adsorbent was again placed in a heated enclosure at 150° C. and maintained at a pressure of 10 psig using back pressure regulators. Toluene desorbent was directed into the columns at a measured rate. A 20 mL pulse of a feed containing 32 mass percent toluene, 9.7 mass percent para-xylene, 14.8 mass percent meta-xylene, 9.4 mass percent ortho-xylene, 9.7 mass percent 1,3,5-trimethylbenzene, 20.0 mass percent 1,2,4-trimethylbenzene, and 4 mass percent 1,2,5-trimethylbenzene was introduced and the desorbent flow was resumed. While in the column, the $C_8$ alkylaromatic hydrocarbons and $C_9$ alkylaromatic hydrocarbons were maintained in the vapor phase. The effluent of the system was condensed and analyzed by gas chromatography to obtain the composition of the effluent. FIG. 6 shows the concentration profiles of the effluent beginning with the background level of toluene desorbent and $C_8$ alkylaromatic hydrocarbons, the background level of $C_8$ alkylaromatic hydrocarbons is due to toluene disproportionation. The concentrations of each individual species in a class were summed and the sum of the concentrations plotted. A region of effluent enriched in $C_8$ alkylaromatic hydrocarbons elutes prior to a region enriched in $C_9$ alkylaromatic hydrocarbons demonstrating that separation of the $C_8$ alkylaromatic hydrocarbons from the $C_9$ alkylaromatic hydrocarbons is occurring.

What is claimed is:

1. A process for producing at least one $C_8$ alkylaromatic hydrocarbon comprising:

a) introducing a feedstock containing at least a benzene or toluene reactant and at least one $C_9$ or $C_{10}$ alkylaromatic hydrocarbon reactant containing at least one methyl or ethyl group to a reactive chromatography fixed bed reaction and adsorption zone comprising a catalyst effective to transalkylate the reactants and provide at least one $C_8$ alkylaromatic hydrocarbon product and an adsorbent effective to selectively adsorb the $C_9$ or $C_{10}$ alkylaromatic hydrocarbon reactant(s) relative to the $C_8$ alkylaromatic hydrocarbon product (s), said zone operating under conditions effective for transalkylation and selective adsorption and having a hydrogen atmosphere such that the mole ratio of hydrogen to hydrocarbon is in the range of about 0.1 to about 6;

b) introducing a desorbent capable of desorbing the $C_9$ or $C_{10}$ alkylaromatic hydrocarbon reactant(s) to a first portion of said zone, and withdrawing an effluent containing at least one product from a second portion of said zone;

c) redirecting, after a period of time, the introduction of the desorbent to the second portion of said zone and concurrently moving the location of the withdrawal of the effluent to the first portion of said zone; and d) continuing alternating the introduction of the desorbent between the first portion and the second portion of said zone while concurrently alternating the withdrawal of the effluent between the second portion and the first portion of said zone.

2. The process of claim 1 wherein the feedstock is introduced in a pulsed mode or in a continuous mode.

3. The process of claim 1 wherein the feedstock is introduced in a pulsed mode to the same portion of the zone as the desorbent is introduced.

4. The process of claim 1 wherein the feedstock is continuously introduced to a location where the reaction and adsorption zone is symmetrically disposed about said feedstock introduction point with respect to the size of the zone, the flow capacity of the zone, and the catalyst and adsorbent distribution.

5. The process of claim 1 wherein the desorbent is benzene, toluene, or a mixture thereof.

6. The process of claim 1 wherein the catalyst is selected from the group consisting of mordenite, zeolite Beta, ZSM-5, dealuminated zeolite Y having a $SiO_2/Al_2O_3$ ratio in the range of from about 5 to about 25, sulfated zirconia, tungstated zirconia, and sulfated and tungstated zirconia.

7. The process of claim 1 wherein the adsorbent is selected from the group consisting of zeolite Beta, zeolite X, zeolite Y, zeolite Y ion exchanged with a metal selected from the group consisting of calcium, sodium, strontium, a Group IB element, a Group VIII element, or mixtures thereof, dealuminated zeolite Y having a $SiO_2/Al_2O_3$ ratio in the range of from about 5 to about 25, dealuminated zeolite Y having a $SiO_2/Al_2O_3$ ratio in the range of from about 5 to about 25 and ion exchanged with a metal selected from the group consisting of calcium, potassium, sodium, strontium, a Group IB element, a Group VIII element, or mixtures thereof, and a combination thereof.

8. The process of claim 1 further characterized by purifying the effluent using fractionation or crystallization.

9. A process for producing at least one $C_8$ alkylaromatic hydrocarbon product comprising:

a) introducing a feedstock containing at least one $C_9$ or $C_{10}$ alkylaromatic hydrocarbon reactant having at least one methyl or ethyl group and a desorbent selected from the group consisting of benzene, toluene, or a mixture thereof, to a reactive chromatography fixed bed reaction and adsorption zone containing a catalyst effective to transalkylate the reactant(s) and desorbent and provide at least one $C_8$ alkylaromatic hydrocarbon product, and an adsorbent effective to selectively adsorb the reactant(s) relative to the $C_8$ alkylaromatic hydrocarbon product(s), said zone operating under conditions effective for transalkylation and selective adsorption and said zone having a hydrogen atmosphere so that the mole ratio of hydrogen to hydrocarbon is in the range of about 0.1 to about 6;

b) introducing said desorbent to a first portion of said zone and withdrawing an effluent containing at least one $C_8$ alkylaromatic hydrocarbon product from a second portion of said zone;

c) redirecting, after a period of time, the introduction of the desorbent to the second portion of said zone and concurrently moving the location of the withdrawal of the effluent to the first portion of said zone; and d) continuing alternating the introduction of the desorbent between the first portion and the second portion of said zone while concurrently alternating the withdrawal of the effluent between the second portion and the first portion of said zone.

10. The process of claim 9 wherein the feedstock is introduced in a pulsed mode or in a continuous mode.

11. The process of claim 9 wherein the feedstock is introduced in a pulsed mode to the same portion of the zone as the desorbent is introduced.

12. The process of claim 9 wherein the feedstock is continuously introduced to a location where the reaction and adsorption zone is symmetrically disposed about said feedstock introduction point with respect to the size of the zone, the flow capacity of the zone, and the catalyst and adsorbent distribution.

13. The process of claim 9 wherein the catalyst and adsorbent are present in the zone as a homogeneous mixture.

14. The process of claim 9 wherein the catalyst is selected from the group consisting of mordenite, zeolite Beta, ZSM-5, dealuminated zeolite Y having a $SiO_2/Al_2O_3$ ratio in the range of from about 5 to about 25, sulfated zirconia, tungstated zirconia, and sulfated and tungstated zirconia.

15. The process of claim 9 wherein the adsorbent in selected from the group consisting of zeolite Beta, zeolite X, zeolite Y, zeolite Y ion exchanged with a metal selected from the group consisting of calcium, sodium, strontium, a Group IB element, a Group VIII element, or mixtures thereof, dealuminated zeolite Y having a $SiO_2/Al_2O_3$ ratio in the range of from about 5 to about 25, dealuminated zeolite Y having a $SiO_2/Al_2O_3$ ratio in the range of from about 5 to about 25 and ion exchanged with a metal selected from the group consisting of calcium, potassium, sodium, strontium, a Group IB element, a Group VIII element, or mixtures thereof, and a combination thereof.

16. The process of claim 9 further characterized by purifying the effluent using fractionation or crystallization.

* * * * *